United States Patent
Miles

(10) Patent No.: US 7,476,646 B1
(45) Date of Patent: Jan. 13, 2009

(54) AGRICULTURAL PROMOTERS/ACTIVE INGREDIENTS

(75) Inventor: David Lucas Miles, Chapel Hill, NC (US)

(73) Assignee: CJB Industries, Inc., Valdosta, GA (US)

( * ) Notice: Subject to any disclaimer, the term of this patent is extended or adjusted under 35 U.S.C. 154(b) by 0 days.

(21) Appl. No.: 11/236,312

(22) Filed: Sep. 27, 2005

Related U.S. Application Data

(60) Provisional application No. 60/613,524, filed on Sep. 27, 2004, now abandoned.

(51) Int. Cl.
*C11D 1/62* (2006.01)
*A01N 65/00* (2006.01)
*A01N 37/00* (2006.01)
*A01N 33/00* (2006.01)

(52) U.S. Cl. .............. 510/504; 510/434; 510/480; 510/477; 510/421; 504/189; 504/320; 504/326

(58) Field of Classification Search ............ 510/382, 510/383, 384, 391, 504, 434, 480, 477, 421; 504/189, 320, 326
See application file for complete search history.

(56) References Cited

U.S. PATENT DOCUMENTS

| | | | |
|---|---|---|---|
| 3,836,669 A * | 9/1974 | Dadekian | 514/642 |
| 3,880,613 A * | 4/1975 | Oswald et al. | 44/394 |
| 3,929,451 A * | 12/1975 | Cross et al. | 504/280 |
| 4,132,780 A | 1/1979 | McConnell | |
| 4,607,036 A * | 8/1986 | Borovian | 514/277 |
| 5,041,275 A * | 8/1991 | Miller | 423/269 |
| 5,124,359 A | 6/1992 | Wachman et al. | |
| 5,180,587 A | 1/1993 | Moore | |
| 5,258,409 A * | 11/1993 | Gay | 514/642 |
| 5,288,483 A * | 2/1994 | Cardin et al. | 514/65 |
| 5,312,558 A | 5/1994 | West | |
| 5,547,918 A | 8/1996 | Newton et al. | |
| 5,547,990 A * | 8/1996 | Hall et al. | 514/563 |
| 5,660,821 A | 8/1997 | Birbara et al. | |
| 5,723,406 A * | 3/1998 | Larose et al. | 504/114 |
| 5,863,909 A | 1/1999 | Kurita et al. | |
| 5,985,794 A * | 11/1999 | Hasebe et al. | 504/362 |
| 5,997,602 A | 12/1999 | Aijala | |
| 6,149,913 A | 11/2000 | Holmes | |
| 6,200,586 B1 | 3/2001 | Lambie et al. | |
| 6,206,946 B1 | 3/2001 | Hayashi et al. | |
| 6,242,526 B1 * | 6/2001 | Siddiqui et al. | 524/555 |
| 6,352,585 B1 | 3/2002 | Diesso | |
| 2003/0224939 A1 * | 12/2003 | Miles | 504/206 |
| 2004/0071653 A1 * | 4/2004 | Bratescu et al. | 424/70.24 |
| 2005/0002964 A1 * | 1/2005 | Bockmuhl et al. | 424/195.17 |

FOREIGN PATENT DOCUMENTS

| | | |
|---|---|---|
| CN | 1095412 | 11/1994 |
| FR | 2440601 | 5/1980 |
| JP | 60004110 A | 1/1985 |
| RO | 105352 | 8/1994 |

OTHER PUBLICATIONS

Database AUAB on WEST, Accession No. 1993-303856, Lisson et al. "Effervescent Toilet Deodorizers-uses liberated carbon dioxide to carry active agent to air and water," AU 9332847, Aug. 12, 1993.
Database JPAB on WEST, Accession No. 1986-059770, "Bathroom liquid detergent composition contg. Surfactanct, hydroxyl polyvalent carboxylic acid and terpenic hydrocarbon solvent," JP 61012789A Jan. 21, 1986.
Russell,"Types of Antimicrobial Agents", Principles and Practice of Disinfection, Preservation and Sterilization, Ch. 2, pp. 21-27, 32-36, 55-56, 75-94, 3rd Ed., Blackwell Sc.
Merianos, "Surface-Active Agents" Disinfection, Sterilization, and Preservation, Ch. 14, pp. 283-320, 5th Ed., Lippincott Williams & Wilkins.

* cited by examiner

*Primary Examiner*—Lorna M Douyon
*Assistant Examiner*—Jaison P Thomas
(74) *Attorney, Agent, or Firm*—Womble, Carlyle Sandridge & Rice, PLLC

(57) ABSTRACT

Quaternary ammonium salts, and compositions including these salts, are disclosed. Also disclosed are methods for protecting plants and crops from microbial and other pests by administering the quaternary ammonium salts, or compositions including the salts, to a plant in need of such treatment. The main component of the quaternary ammonium salts is alkyltrimethylammonium chloride or dimethyldialkylammonium chloride, where alkyl is derived from soya, coconut, cottonseed, tallow, or hogfat fatty acids or the individual ammonium salts isolated therefrom.

6 Claims, No Drawings

AGRICULTURAL PROMOTERS/ACTIVE INGREDIENTS

This application claims benefit of U.S. Provisional Application No. 60/613,524, filed on Sep. 27, 2004, now abandoned.

FIELD OF THE INVENTION

The present invention relates generally to quaternary ammonium compounds ("QACs or quats"), and more specifically, to alkyltrimethylammonium and dimethyldialkylammonium chlorides, where the alkyl groups are derived from soya, coconut, cottonseed, tallow, or hogfat fatty acids or the individual ammonium salts contained therein.

BACKGROUND OF THE INVENTION

Certain quaternary ammonium compounds ("QACs" or "quats") are known for their bactericidal and fungicidal activity, especially on hard surfaces. Benzalkonium chloride (BAC) is one of the most widely used biocides used in the market. Benzalkonium chloride is the generic name (by the Official United States Pharmacopia) for a pharmaceutical aid. The USP specification indicates that 70% minimum of the total alkylbenzyldimethyl ammonium chloride contents are C12/C14 homologues. The number of homologues that were evaluated to get to that combination of molecules required an incredible amount of work and research time, and that was just the first generation of QACs. Modification of the benzene ring with different alkyl and halide groups led to a second generation of substituted benzalkonium chlorides. A third generation resulted from the evaluation of dialkyldimethylammonium chlorides. These were by far of the greatest commercial significance. The fourth generation of quaternary ammonium compounds was brought on in 1965 by a technological breakthrough. Catalytic amination of long chain alcohols made possible the production of dialkylmethylamines, which react with methylchloride to make twin chain quaternary ammonium compounds such as didecyldimethylamonium chloride and dioctadecylydimethyl ammonium chloride. Research then branched in other directions, such as using N-laurylpyridinium and blends of different generations of quats. The fourth generation quats products showed an outstanding bactericidal performance, good tolerance for anionic surfactants, proteins loads, hard water and did not cause as many foam problems.[1] (Ref R)

QACs are primarily active against Gram-positive bacteria, whereas in agriculture almost all of the significant bacterial diseases are Gram-negative. At higher concentrations, quats are bactericidal towards Gram-negative bacteria, but some strains are quite resistant. Viruses are even more resistant, even though certain quats exhibit virucidal activity against many lipophilic viruses.(Ref S). Bond in 1995 (Ref S) suggested that a crucial aspect of quats' activity against HIV and the hepatitis B virus (HBV) was due to the absence of organic matter. As agriculture is full of organic matter, Bond would seem to suggest that quats are relatively inactive against viruses in agriculture. Quats are also known to be fungistatic, and not fungicidal (Ref S).

QACs are known to be incompatible with a wide range of chemical compounds, including anionic surfactants, and nonionic surfactants such as lubrols, tweens, and phospholipids such as lecithin found in soybean oil and other fat containing materials.(Ref S) Smolka did report that some QACs can be activated by nonionic surfactants. The antimicrobial activity of the QACs is greatly altered by organic matter, including milk, serum, and feces, which reduce their activity.

QACs are used in food hygiene, in hospitals, as a soak for hard contact lenses, and some are used to treat small wound surfaces, shampoos, and cosmetics. They have been used in the veterinary field to clean and disinfect automatic calf feeders, and in sheep dips, but they are not used in large amounts on farms, presumably due to the organic debris they are going to encounter (Ref S). In general, QACs are effective preservatives for pharmaceuticals and disinfectants for hard surfaces.

However, efficacy studies (Ref 1, 2) suggest considerable differences between BACs and other known QACs. On Staphylococcus, BACs are about 2.5 as effective as other QACs tested. On contact lenses they are about 6 times as effective. They are primarily active against gram-positive bacteria. They are also fungistatic and not fungicidal. The activity of QACs is affected greatly by organic matter. They are used for contact lenses, skin disinfection, deodorants, shampoos, and controlling algae in swimming pools. There are products on the market based on BAC used for controlling bacteria and fungus on turf and ornamental plants, but problems with phytotoxicity and environmental concerns have kept it from being used in agriculture. QACs are phytotoxic and many are cytotoxic as well. BAC is over 100 times as cytotoxic as other QACs, so there can be large differences in not only activity, but cell death from different QACs.

It would be advantageous to develop quaternary ammonium compounds other than BACs which are microbiocidally effective against the type of microbes present in agriculture, and which do not lose their potency in the presence of organic matter, such as that present in agriculture. The present invention provides such quaternary ammonium compounds, and methods of treating crops, plants, swimming pools and the like using the compounds.

SUMMARY OF THE INVENTION

The present invention provides quaternary ammonium compounds that have many of the advantages of QACs known in the art, but without many of their detriments. Agricultural compositions including the compounds, and methods of treating a crop locus or a plant using the compositions, are also disclosed. Further, methods of soil conditioning, soil injection, and treatment of pools are also disclosed.

The QAC compounds are alkyltrimethyl and dialkyldimethyl ammonium chlorides, with dialkyldimethyl ammonium chlorides being preferred, where the alkyl groups are $C_{8-16}$ alkyl groups. These alkyl groups can optionally be substituted with one or more substituents commonly present in QAC compounds. Unlike the BACs known in the prior art, these compounds are effective against fungi and bacteria, in agriculture use.

The QAC products described herein are environmentally acceptable and can be used to provide protection from fungi, bacteria, viruses, and other pests that adversely affect agricultural products and plants. The products can be provided slow release forms to administer the antimicrobial QACs to plants in a controlled manner. Alternatively, the QACs can be applied directly on the plants by foliar treatment. This provides quicker and more efficient protection, while not being phytotoxic. The QAC products can be used alone, or in combination with other active ingredients.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description. The invention is capable of other embodiments and of being practiced and carried out in various ways. Also, it is to be understood that the phraseology and terminology employed herein are for the purpose of the description and should not be regarded as limiting.

Other objects and advantages of the present invention will become obvious to the reader and it is intended that these objects and advantages are within the scope of the present invention.

DETAILED DESCRIPTION OF THE INVENTION

The quaternary ammonium compounds described herein, the agricultural compositions including the compounds, and the methods of using the compounds and compositions, will be better understood with reference to the following non-limiting detailed description.

I. Quaternary Ammonium Compounds

The quaternary ammonium compounds described herein are long chain alkyl trimethyl and dialkyl dimethyl ammonium chlorides, where the alkyl groups are $C_{8-16}$ straight chain, branched or cyclic alkyl groups. The alkyl groups can optionally be substituted with one or more substituents, for example, from one to three substituents, selected from hydroxyl, carboxy, thiol, amine, halo, oxo, phosphate, phosphite, sulfate, nitrile, nitro, amide, alkoxy, thioalkoxy, ester, and the like, where any alkyl groups present on the substituents are generally $C_{1-6}$ alkyl groups.

Examples of QACs that are useful include alkyltrimethylammonium and dimethyldialkylammonium chlorides, where alkyl group(s) is/are derived from soya, coconut, cottonseed, tallow, or hogfat fatty acids or the individual ammonium salts isolated therefrom.

II. Agricultural Compositions Including the Compounds

The compounds can be included in virtually any agricultural composition commonly applied to plants. They can also be combined with other agricultural compounds, such as plant growth regulators and the like.

The compositions or products described herein can be supplied as a solid or a liquid, including thixotropic droplets. The solid can be a granule or a powder. The liquid can be a solution, dispersion or suspension in water or other carrier. These products are generally diluted into water before being sprayed onto the field from either an airplane or ground application equipment. However, other water-miscible solvents can also be used, typically in concentrations of less than 25% by volume. These solvents include, but are not limited to, $C_{1-5}$ alcohols such as ethanol, propanol and isopropyl alcohol, polyhydric alcohols such as glycerol, pentaerythritol, and the like, dimethyl sulfoxide, dimethyl formamide, glymes, acetone and the like. Crop oils can also be used.

The liquid compositions described herein can be prepared by methods known in the art. Useful emulsion formulations will not separate into oil and water phases during extended storage at ambient temperatures. To enhance stability, the particle size of the emulsion particles may be reduced by techniques known in the art such as shearing, and the use of surfactants and/or thickeners.

Other compounds can add to the efficacy to help provide the boost in activity in some cases where the activity of the quaternary ammonium compound is challenged, such as by gram negative bacteria which cause many of the diseases found in agriculture.

Any type of agricultural chemical, pesticide or genetic material, which results in a desired effect on a plant and which does not adversely effect the useful properties of the quaternary ammonium compound can be used in combination with the quaternary ammonium compounds. The active components can be herbicidal, pesticidal, insecticidal, bactericidal, virucidal, fungicidal, acaricidal, and the like. The active components can be genetic material to be transfected into a plant. Examples of suitable active agricultural compounds that can also be used in conjunction with the quaternary ammonium compounds described herein are described in more detail below.

Such compounds include chelating agents, and mixtures of thereof. The chelating agents add to, or in some cases, synergize the activity. Generally, useful chelating compounds include, but are not limited to sugars, amino acids, organic diacids, diamines, alpha ketoacids, alphahydroxyacids, aminodiacids, amino triacids, amino tetraacids, tdol aminees, and organic polyacids and their sodium, potassium, and ammonium salts. Specific examples of these chelating compounds include, but are not limited to the sugars, acids and salts of maleic acid, malonic acid, tartaric acid, citric acid, glycine, lactic acid, malic acid, succinic acid, oxalic acid, dextrose, ethylenediaminetetraacetic acid (EDTA), tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine, sodium polyphosphate, potassium polyphophate, ammonium polyphosphate, sodium hexametaphosphate and mixtures thereof. The chelating agent used in the present compositions can be 100% of any particular chelator, or a combination of chelator in any ratio. A combination or mixture of chelating compounds may dissolve faster than a single compound. EDTA is extremely effective in providing an increase in activity toward gram negative bacteria. Phenols, amines such as tris, DMDC, HMDA and hexadecylamine also add to and/or synergize the activity Examples of particularly useful primary alkylamines include those where the alkyl group is derived from coconut, cottonseed, soya or tallow, and also include hexamethylenetetramine and EDTA.

Stickers, such as thixotropic agents, are useful for providing an increase in activity by holding the quaternary ammonium compound in a protective position on the leaf, stem, or other surface to be protected. Stickers can be based on terpenes, drying oils, vegetable oils, and latexes or other polymer solutions or emulsions.

Surfactants, ideally used at a proper use rate and at the proper level (as known to those of skill in the art), can also boost activity. Representative surfactants include alkylphenol ethoxylates, silicone surfactants and sorbitan oleates.

When the compounds are included in an emulsion, it can be advantageous to include in any such emulsion formulation a compound or mixture of compounds which stop or slow the separation of the formulation. Representative suspension aids include guar and modified guar gums, xanthan gum, acacia gum, bentonite, hormite or smectite clays, cellulose and modified cellulose gums, tragacanths, carageenan, polyacrylates, sodium alginates and carbomers, but can also include other compounds known to raise viscosity. Also important to the stability of an emulsion formulation is the particle size. As the QAC formulations can be composed of oils and water, the particle size of the emulsion is preferably reduced such that separation will be slowed. Particle sizes less than 10 microns are preferred, and in general the smaller the particle the slower the separation rate.

Other components that can be used in these formulations include antifoams, such as silicone emulsions, alcohols, hydrocarbons, glycerine oleate, or polyalkalene glycols or combinations thereof. Compounds which aid with freeze thaw stability, such as propylene glycol or glycerine, can also be used. Another optional, but preferred component is a biocide such as methyl, propyl, or butyl paraben, 1,2 benzisothiazolin-3-one, potassium sorbate, or ascorbic acid. Other suitable biocides may be used as well.

A pesticide is defined by the Federal Government in 40 CFR 152.3 as "any substance (or group of structurally similar substances if specified by the Agency) that will prevent, destroy, repel, or mitigate any pest, or that functions as a plant regulator, desiccant or defoliant within wording the meaning of FIFRA sec. 2 (a)." Several types of pesticides are described in more detail below.

Plant Growth Regulators

Any compound that regulates plant growth can be included in the compositions of the invention. Examples of the plant-growth regulator include defoliators and desiccants. Specific examples include MH (maleic hydrazide), ethephon (2-chloroethylphosphonic acid), Folek (S,S,S, tributyl phosphorothioate, Dropp (thidiazuron), Pix (mepiquat chloride). Any defoliating compound that is effective at defoliating a desired plant can be used. Examples of suitable defoliating agents include paraquat, diquat, endothall, chlorates, ethephon, tributylphosphorthoate, cacodylic acid and its sodium salt, MSMA, diuron, dimethipin, monocarbamide, carfentrazone, cyclanalide and thidiazuron.

The quaternary ammonium compound application rate used in the current method ranges from about 0.01 pound per acre to about 5 pounds per acre, preferably from about 0.25 to about 2.5 pounds per acre. The quaternary ammonium compound can be used and/or applied with paraquat, diquat, endothall, chlorates, ethephon, tributylphosphorothioate, cacodylic acid and its sodium salt, MSMA, diuron, dimethipin, monocarbamide, carfentrazone, cyclanalide and thidiazuron in ratios from 1:100 to 100:1, preferably from 1:10 to 10:1.

Herbicides

Any herbicide that causes the desired result can be used. Herbicides are generally broken down into broad categories, including pre-plant herbicides, burndown herbicides, and post-emergence herbicides. Those of skill in the art of farming know when it is appropriate to use a particular type of herbicide.

There are several classes of post-emergent herbicides. These include:

A. Downwardly Mobile Herbicides [Symplastically Translocated (leaf to growing points)]
1. Auxin Growth Regulators
Phenoxy
Benzoic acid derivatives
Picolinic acid derivatives
2. Amino Acid Inhibitors (aromatic)
Glyphosate
Sulfosate
3. Amino acid inhibitors
Sulfonyl Ureas
Imidazolinones
Sulfonanalides
4. Pigment Inhibitors
5. Grass Meristem Destroyers (Lipid Biosynthesis Inhibitors)
Aryloxyphenoxypropionates
cyclohexanediones
B. Non Translocated (Contact Herbicides)
1. Cell Membrane Destroyers
Bipyridyliums
Diphenyl ethers (nitrophenyl ethers)
C. Upwardly Mobile Only Herbicides (Apoplastically Translocated)
1. Photosynthetic Inhibitors
Triazines
Uracils
Phenylureas
Nitriles Examples of acid amide-based herbicides include Stam (3',4'-dichloropropionanilide, DCPA) and Alachlor (2-chloro-2',6'-diethyl-N-(methoxymethyl)-acetanilide). Examples of urea-based herbicides include DCMU (3-(3,4-dichlorophenyl)-1,1-dimethylurea) and Rinuron (3-(3,4-dichlorophenyl)-1-methoxy-1-methylurea). Examples of sulfonyl urea-based herbicides include thifensulfuronmethyl (methyl-3-(4-methoxy-6-methyl-1,3,5-triazin-2-ylcarbamoylsulfamoyl)-2-tanoate) and Flazesulfuron (1-(4,6-dimethoxy pyrimidin-2-yl)-3-(3-trifluoromethyl-2-pyridylsulfonyl)urea). Examples of dipyridyl-based herbicides include Paraquat dichloride (1,1'-dimethyl-4,4'-bipyridinium dichloride) and Diquat dibromide (6,7-dihydrodipyride[1,2-a:2',1'c]-pyrazinedium dibromide). An example of a diazine-based herbicide is Bromacil (5-bromo-3-sec-butyl-6-methyluracil). Examples of S-triazine-based herbicides include Gesatop (2-chloro-4,6-bis(ethylamino)-1, 3,5-triazine) and Simetryn (2,4-bis(ethylamino)-6-methylthio-1,3,5-triazine). An example of nitrile-based herbicides include DBN (2,6-dichlorobenzonitrile-). Examples of dinitroaniline-based herbicides include Trifluralin (alpha, alpha, alpha-trifluoro-2,6-dinitro-N,N-dipropyl-p-toluidine).

Examples of carbamate-based herbicides include Thiobencarb (Saturn) (S-p-chlorobenzyl diethylthiocarbamate) and MCC (methyl-3,4-dichlorocarbenzylate. NIP (2,4-dichlorophenyl-p-nitro-phenyl ether) is an example of diphenyl ether-based herbicides. PCP (sodium pentachlorophenoxide) is an example of a phenol-based herbicide. MDBA (3,6-dichloro-2-methoxybenzoic acid dimethylamine salt) is an example of a benzoic acid-based herbicide. Examples of phenoxy-based herbicides include 2,4-D sodium salt (sodium 2,4-dichlorophenoxyacetate), 2,4 D Esters, and Mapica ([4-chloro-o-toluoyl)oxy]aceto-o-chloroanilide. Examples of organic phosphorus-based herbicides include Glyphosate (N-(phosphonomethyl) glycinate, Bialaphos (sodium salt of L-2-amino-4-[(hydroxy(methyl)phosphinoyl]-butyl)-l-alanyl-N-alanine), and Glufosinate (ammonium DL-homoalanin-4-yl (methyl) phosphinate). TCA sodium salt (sodium trichloronate) is an example of an aliphatic group-based herbicide. Hydrogen peroxide is another herbicide.

Among these herbicides, the dipyridyl-based herbicides and the organic phosphorus-based herbicides are preferred. Among them, the organic phosphorus-based herbicides are more preferred, and Bialaphos (sodium salt of L-2-amino-4-[hydroxy)(methyl)phosphinoyl]-butyl-L-alanyl-N-alanine), Glufosinate (ammonium DL-homoalanin-4-yl(methyl) phosphinate), or Glyphosate (N-(phosphonomethyl) glycinate) are particularly preferred.

Insecticides

Any insecticide that is effective against a particular insect to be eliminated from a particular crop or site can be used.

Examples of pyrethroid type insecticides include Fenvalerate (alpha-cyano-3-phenoxybenzyl-2-(4-chlorophenyl)-3-methylbutanoate) and Baythroid (cyano-4-fluoro-3-phenoxybenzyl-3-(2,2-dichlorovinyl)-2,2-dimethylcyclopropanecarboxylate). Organic phosphorus type insecticides include DDVP (2,2-dichlorovinyldimethyl phosphate), Sumithion (MEP) (dimethyl 4-nitro-m-tolyl phosphorothioate), Malathion (S-1,2-bis(ethoxycarbonyl)ethyldimethyl phosphorodethioate), Dimethoate (dimethyl S-(N-methylcarbamoylmethyl) phosphorodithioate), Elsan (S-[alpha-(ethoxycarbonyl)benzyl] dimethyl phosphorodithioate), and Baycid (dimethyl 4-methylthio-m-tolyl phosphorothioate). Carbamate type insecticides include Bassa (O-sec-butylphenyl methylcarbamate), MTMC (m-tolylmethylcarbamate), Meopal (3,4-dimethylphenyl-N-methylcarbamate), and NAC (1-naphthyl methylcarbamate), and Methomyl (S-methyl-N-(methylcarbamoyloxy)thioacetimidate), and Cartap (SS'-2-dimethylamino trimethylene bis-(thiocarbamate)), for example. Natural insecticides include pyrethrin preparations and piperonyl butoxide preparations which originate from Chrysanthemum cinerariaefolium, rotenone preparations, which originate from Derris which is a shrub of the pulse family, and nicotine (3-(1-methyl-2-pyrrolidinyl)pyridine sulfate) preparations originating in derris shrubs of Family Legumoinosae. Examples of the insect growth regulators (IGR), Diflubenzuron (1-(4-chlorophenyl)-3-(2,6-difluorobenzoyl)urea), Teflubenzuron (1-[3,5-dichloro-2,4-difluorophenyl)-3-(2,6-difluorobenzoyl)urea, Chlorfluazuron (1-[3,5-dichloro-4-(3-chloro-5-trifluoromethyl-2-pyridiloxyphenyl]-3(2,6-difluorobenzoyl)urea, Buprofezin (2-tert butylimino-3-isopropyl-5-phenyl-3,4,5,6-tetrahydro-2H-1,3,5-thiadiazin-4-one), and Fenoxycarb (ethyl 2-(4-phenoxyphenoxy)ethylcarbamate).

Bactericides, Fungicides and Virucides

Any bactericide, fungicide or virucide that is effective at a particular bacteria, fungus or virus can be incorporated into the compositions described herein and applied to a desired crop or situs. Examples of suitable bactericide and fungicides include Dithane (zinc ethylenebis(dithiocarbamate)), Maneb (manganese ethylenebis(dithiocarbamate)), Thiram (bis(dimethylthiocarbamoyl) disulfide) Manzeb (complex of zinc and manganese ethylenebis(dithiocarbamate), Bisdithane (bisdimethyl dithiocarbamoyl zinc ethylene bisdithiacarbamate), and Propineb (polymeric zinc propylenebis(dithiocarbamate), benzimidazole-based fungicides including Benomyl (methyl 1-(butylcarbamoyl)-2-benzimidazole carbamate) and Thiophanate-methyl (dimethyl(4,4'-o-phenylenebis(3-thioallophanate)), and Vinclozolin (3-(3,5-dichlorophenyl)-5-methyl-5-vinyl-1,3-oxazolidine-2,4-dione), Iprodione (3-(3,5-dichlorophenyl)-N-isopropyl-2,4-dioxoimidazolidine-1-carboxamide), Procymidone (N-(3,5-dichlorophenyl)-1,2-dimethylcyclopropane-1,2-dicarboximide), Anilazine (2,4-dichloro-6-(o-chloroanilino)-1,3,5-triazine), Triflumizole ((E)-4-chloro-alpha, alpha, alpha-trifluoro-N-(1-imidazol-1-yl-2-propoxyethylidene)o-toluidine), Metalaxyl (methyl-N-(2-methoxyacetyl)-N-(2,6-xylyl)-DIL-alaninate), Bitertanol (all-rac-1-(biphenyl-4-yloxy)-3,3-dimethyl-1-(1,2,4-triazol-1-yl)butan-2-ol), Pyrifenox (2',4'-dichloro-2-(3-pyridyl)acetophenone-(EZ)-O-methyloxime), Fenarimol (2,4'-dichloro-.alpha.-(pyrimidin-5yl)benzhydrylalcohol), Triforine (1,4-bis-(2,2,2-trichloro-1-formamidoethyl)-piperazine), Guazatine iminoctadine (1,1-iminodi(octamethylene) diguanidinium triacetate), Oxine-copper, copper sulfate, copper chloride, copper oxychloride, copper carbonates, copper oxalates, copper acaetate, copper hydroxide, copper oxides, copper phosphates, copper silicates, copper napthenate, copper oleate, copper quinolinolate and copper resinate, Bordeaux mixture, antibiotic bactericides (streptomycin type, tetracycline type, polyoxins type, blasticidin S type, kasugamycin type, and validamycin type),phenols, organic and inorganic acids, esters, and salts (acetic acid, propionic acid, undecanoic acid, sorbic acid, lactic acid, benzoic acid, salicylic acid, dehydroacetic acid, sulfur dioxide, sulfites, parabens, and vanillic acid esters) aldehydes (formaldehyde and formaldehyde releasers, benzaldehyde, cinnimaldehyde, and glutaraldehyde) Triadimefon (1-(4-chlorophenoxy)-3,3-dimethyl-1-(1, 2,4-triazol-1-yl)-2-butanone), Isoprothiolane (diisopropyl-1, 3-dithiolan-2-ylidenemalanate), Daconil (tetrachloroisophthalonitrile), Pansoil (5-ethoxy-3-trichloromethyl-1,2,4-thiadiazole), Fthalide (4,5,6,7-tetrachlorophmalide), Kitazin-P (0,0-diisopropyl-phosphorothioate), Hinosan (ethyl S,S-diphenylphosphorodithioate), Probenazole (3-allyloxy-1,2-benzisothiazol 1,1-dioxide), hydrogen peroxide, essential oils, Captan (N-(trichloromethylthio)-4-cyclohexene-1,2-dicarboximide), and Fosetyl (aluminum tris (ethylphosphonate)).

Acaricides

Any suitable acaracide can be used. Examples of suitable acaricides include Sumiito (2-tert-butyl-5-(4-tert-butylbenzylthio)-4-chloropyridazine-3-(2H)-one), Acricid (2,4-dinitro-6-sec.-butylphenyldimethylacrylate), Chloromite (isopropyl 4,4-dichlorobenzylate), Akar (ethyl 4,4'-dichlorobenzilate), Kelthane (2,2,2-trichloro-1,1-bis(p-chlorophenyl)ethanol), Citrazon (benzoic 3-chloro-N-ethoxy-2,6-dimethoxybenzimidic anhydride), Omite (2-(p-tert-butylphenoxy)cyclohexyl propyn-2-yl sulfite), Osadan (bis[tris(2-methyl-2-phenylpropyl)tin]oxide), Hexythiazox (trans-5-(4-chlorophenyl)-N-cyclohexyl-4-methyl-2-oxothiazolidine-3-carbox amide), and Amitraz (N,N-bis(2,4-xylyliminomethyl)methylamine).

Wood Treatment Chemicals

Any wood treatment chemical capable of inhibiting destruction of wood by termites, fungus, mold and the like can be used. Examples of suitable wood treatment chemicals include CCA, polyethylene glycol, fungicides, termiticides, and known fungicides.

Pool Chemicals

Any chemicals used to treat pools can also be used, particularly in those embodiments where the QACs are used in methods for treating pool water to remove microbiocidal contaminants.

III. Methods of Using the Compounds

The compounds are effective against fungi and bacteria, in agriculture (i.e., are microbiocidal). The compounds can be mixed with water, or other carrier liquids used in the art of agricultural chemistry, and applied to plants in a microbiocidally effective dosage.

The compounds, or agricultural compositions including the compounds, can be applied to plants to provide protection from fungal and bacterial diseases, as well as algae and some viruses. Dips and drenches may be used as well. At typical use rates, the compounds are not phytotoxic.

Particularly when the compounds are mixed into an oil or an emulsion, the compounds can be applied by spraying or crop dusting.

When applied to a tree, the compounds or compositions can be applied by injection into the trunk. When applied to a crop locus, or to an individual plant, the compounds or compositions can be applied by irrigation, foliar application, root application, overhead spray, by air, or by ground.

Examples of crops/plants that can be treated include almond trees, and grape vines, to treat xylum limited infection. For example, the compounds can be injected right into the xylum of the tree to treat and/or prevent the infection.

Tomatoes, peppers, fruit trees, celery, cucurbits, grapes, almonds, and beans, generally, such as green beans, which often suffer from bacterial infection, can be treated using the compounds and compositions described herein. This treatment can be particularly advantageous where known bactericidal compounds, such as copper oxytetracycline, do not work well, and where bacterial resistance to streptomycin has been developed. Such bacterial infections have often lead to certain crops, such as beans, only being grown in selected regions.

The compounds can also be used in antifungal applications. For example, fungal infections on grapes, and brown patch on grass and ornamentals, can be treated. In particular, major fungal pests which can be treated using the compounds and compositions described herein include phytophora alternaria and colletotrichum, which cause summer decline of turf grass.

Most plants such as grasses, alfalfa, turf, soybeans (which suffer from soybean rust), peanuts, potatoes, stone fruits such as peaches, plums and cherries, apples, pears, wheat (which suffers from smuts, strips and rusts), cucurbits, vegetables, tomatoes, and peppers are examples of plants that are often prone to fungal infection, and thus amenable to treatment and/or prevention of fungal infection using the compounds and compositions described herein.

Viral infections, such as tobacco mosaic virus and yellow leaf curl (which primarily affects tomato plants), can also be treated using the compounds and compositions described herein.

The compounds can also be used in soil conditioning or soil injection, to replace the methyl bromide that is commonly used. This is particularly advantageous, since contact with methyl bromide is associated with significant and harmful physiological effects.

The compounds can also be used in pool treatment applications, where the microbes present in pool water can be treated. The compounds tend to be milder to swimmers than the chlorinated compounds commonly used, and can be equally or even more effective.

In another embodiment, the compositions are used to treat a plant with a pesticide, herbicide, insecticide, fungicide, virucide, bacteriocide, and/or acaricide. The methods involve applying to the plant an effective pesticidal, herbicidal, insecticidal, fungicidal, virucidal, bacteriocidal, and/or acaricidal amount of a composition including a permeabilizing agent and a pesticide, herbicide, insecticide, fungicide, virucide, bacteriocide, and/or acaricide.

The formulations described herein can also be used to enhance the results obtained with conventional weed control formulations. Weed control essentially involves applying a compound that selectively controls one type of plant in the presence of another. Examples include crabgrass-selective compounds that have little or no effect on grass. Weed control agents can be combined with the permeabilizing agents described herein to form enhanced weed control agents, enhanced due to their ability to permeate through the cell walls of the undesired weeds. In all of these embodiments, the chelating agents are typically the sugars, acids and salts of maleic acid, malonic acid, tartaric acid, citric acid, glycine, lactic acid, malic acid, succinic acid, oxalic acid, dextrose, ethylenediaminetetraacetic acid (EDTA), tris(hydroxymethyl)aminomethane, lactose, mannitol, glutaric acid, malic acid, succinic acid, glycerol, humic acid, fulvic acid, sorbic acid, sorbose, ethylene diamine, 1,2 diaminocyclohexane, trimethylenediamine, tetramethylenediamine, 1,2 diaminopropane, diethylenetriamine, triethylenetetramine, triaminodiethylamine, N-hydroxyethylethylenediamine-, some quaternary ammonium salts, dimethyl amines, and agriculturally acceptable salts thereof, and mixtures thereof.

The present invention will be better understood with reference to the following non-limiting examples.

EXAMPLE 1

Effect of Quat Salts on Erwinia Carotovora, a Bacterium Affecting Plants

To measure the antibacterial effectiveness of the quat salts, the effect of various salts, at an application rate of 50 ppm, was measured. The data regarding the effectiveness is summarized below:

| Quat Type of Erwinia carotovora at an application rate of 50 ppm | Percent Inhibition |
| --- | --- |
| Cocoalkyltrimethyl ammonium chloride | 25 |
| Soyalkyltrimethyl ammonium chloride | 35 |
| Tallowalkyltrimethyl ammonium chloride | 30 |
| Ditallow dimethyl ammonium chloride | 50 |
| Dicoco dimethyl ammonium chloride | 75 |

The effectiveness of lower concentrations of the quat salts at inhibiting Erwinia carotovora infection was also measured, where various additives were also added. The data is summarized below.

| Effect of Additives of Erwinia carotovora at 30 ppm with dicoco dimethyl ammonium chloride Additive (level) | Percent Inhibition |
| --- | --- |
| None | 40 |
| EDTA (3x quat) | 80 |
| Citric Acid (3x quat) | 60 |
| Oxalic acid (3x quat) | 60 |
| Soyamine (10% quat) | 50 |
| Coco dimethylamine (10% quat) | 60 |
| Calcium Chloride (3x quat) | 60 |
| Magnesium Chloride (3x quat) | 50 |
| EDTA (2.5x) + citric (1x) + soyamine (10%) | 90 |

The data show that the addition of various additives, such as chelating agents, calcium or magnesium ions, or fatty amines, can have a beneficial effect on the antibacterial activity of the quat salts.

EXAMPLE 2

Effect of Sticker on Residual Activity

In order to evaluate the residual activity of the quat salts, the salts were combined with a "sticker" which helps keep the salts on the plants to which they are applied for a relatively longer period of time.

Dollar spot is a disease of turfgrasses caused by the fungus Sclerotinia homeocarpa, which attacks most turfgrasses grown in the South. Bentgrass, hybrid bermudagrasses and zoysia are most susceptible to dollar spot. The disease occurs from spring through fall, and is most active during moist periods of warm days (70-85° F.) and cool nights (60° F.) in the spring, early summer and fall. The disease is spread from one area to another by water, mowers, other equipment or shoes.

The effect of the quat salts described herein at treating dollar spot on turf was evaluated. One treatment involved the application of 400 ppm dicocodimethylammonium chloride, 1200 ppm EDTA, 400 ppm citric acid, and 40 ppm soyamine to turf. A second treatment involved the application of 400 ppm dicocodimethylammonium chloride, 1200 ppm EDTA, 400 ppm citric acid, 40 ppm soyamine, 3000 ppm soybean oil and 180 ppm Tergitol NP-6 (a wetting agent, emulsifier, stabilizer) to turf.

Treatment 1—400 ppm Dicocodimethylammonium chloride+1200 ppm EDTA+400 ppm Citric acid+40 ppm soyamine Treatment 2—400 ppm Dicocodimethylammonium chloride+1200 ppm EDTA+400 ppm Citric acid+40 ppm soyamine+3000 ppm soybean oil+180 ppm Tergitol NP-6

| Disease Control | | | | |
|---|---|---|---|---|
| | Treatment Week | | | |
| | 1 | 2 | 3 | 4 |
| Std - No treatment | 63% | 57% | 65% | 70% |
| Treatment 1 No Sticker | 96% | 95% | 75% | 69% |
| Treatment 2 W Sticker | 100% | 98% | 99% | 98% |

The results show that, while the treatment without a "sticker" is very effective, the residual effect of the quat salts can be augmented by using a sticker.

EXAMPLE 3

Bacterial/Fungal Control

In order to demonstrate the broad activity of the quat salts against a variety of bacterial and fungal infections, laboratory petri dishes with potato agar were provided with various bacteria or fungi. A composition including 5% dicocodimethylammonium chloride, 15% EDTA, 3% citric acid+0.5% soyamine by weight was prepared, and applied at various concentrations to the petri dishes.

The effectiveness of the composition (% inhibition) was measured at 2 days for bacteria, and 4 days for fungi. The results are tabulated below.

| | % Inhibition - 2 Days for bacteria 4 days for fungi Dilution | | |
|---|---|---|---|
| Bacteria/Fungi | 1:1000 | 1:500 | 1:250 |
| *Erwinia* | 33% | 100% | 100% |
| *Pseudomonas* | 100% | 100% | 100% |
| *Xanthomonas* | 57% | 100% | 100% |
| *Botrytis* | 47% | 48% | 84% |
| *Phytophthera* | 100% | 100% | 100% |
| *Rhizoctonia* | 57% | 63% | 71% |
| *Pythium* | 100% | 100% | 100% |

EXAMPLE 4

Field Control

In order to demonstrate the effectiveness of the quat salts at controlling infections in a field test, a composition including 400 ppm dicocodimethylammonium chloride, 1200 ppm EDTA, 400 ppm citric acid, 40 ppm soyamine, 3000 ppm soybean oil, and 180 ppm Tergitol NP-6 was prepared. This composition was applied to a field to which other treatments had been applied. The conditions under which this field control was studies are summarized below.

| Field Control | |
|---|---|
| Crop Planted: | May 26, 2005 |
| # Of previous treatments: | 10 |
| Rotation: | Kocide, Diathane, Oxidate, Ridomil Bravo |
| Fungicide Rotation intervals: | Every 5-7 days |
| Rain Amount during trial: | Over 4.5" over 7 days |
| Average Daytime Temperature: | 90° F. |
| High Temperature: | 99° F. |
| Low Temperature: | 84° F. |

Treatment—400 ppm Dicocodimethylammonium chloride+1200 ppm EDTA+400 ppm Citric acid+40 ppm soyamine+3000 ppm soybean oil+180 ppm Tergitol NP-6

Day 1:

The field was visited the day of application for a pre-spray disease rating. Major problems were observed, and minor problems were observed as well. Ratings were made on the major diseases Bacterial Spot, Grey Mold, Blight, and Leaf Spot. The observations and % ratings were also taken for Rhizoctonia, Powdery Mildew, Stem Rot, and Bacterial Speck.

Bacterial Spot was a big problem. It was obvious and present on at least 40% of the plants. Blight was at least 20%. The other diseases were "growing quickly."

Growth of the plants was stunted. The disease pressure was so heavy that the plants were spending their time protecting themselves and not growing. The plants measured out at 29" (on average) at the start of the trial.

There was considerable ground erosion due to heavy rainfall and high winds had pushed over many plants. Washout was present on all sloped rows, with many plants on their sides due to running water pushing them over. There was also considerable wind stress/burn.

The condition of the field was very poor. The trial was sandwiched between rainstorms with about 10 hours between them to allow the fields to dry. The storms dumped an inch of rain in a half hour period.

The quat salt treatment was applied at a rate of 1 gallon of the composition/100 gallons of water/acre. This relatively low treatment rate provided some concerns regarding complete coverage due to the low volume of water and bushiness of the plants. Blight and Stem Rot were both located at the lower portion of the plant and concealed by a lot of foliage.

Diathane was the last product applied, and was applied 5 days before the start of the trial.

Day 4:

Four plants had been marked on day 1 so that their progress could be tracked both in terms of growth and disease control. All four had grown between 5 and 7 inches in height with a tremendous amount of flowering and new growth present.

On old growth, the yellow halos present when Bacterial Spot is active were dramatically reduced. Due to the high winds and continual rainfall, most of the brown dead spots on the leaves due to Bacterial Spot were punched out and empty. On new growth there was no Bacterial Spot present.

The most noticeable effect was the eradication of Blight. The yellow leaves observed on Day 1 were now brown and curled up. Interestingly, there was no new growth of Blight, making the plant look like it was missing a skirt. The plants where Blight was bad were now doing well a foot off the ground with no green below.

Grey mold was gone, and Powdery Mildew was non-existent as well. However, the effect on Stem Rot was not as complete, as it is difficult to get inside the plant to the stem due to its maturity. The Stem Rot problem was rated at 50% successful at this point.

Rain had done additional damage, and high winds associated with a thunderstorm the night before stressed some old growth. Photos of the stress were taken (not shown) so that it could be determined whether there was any difference at the 7-day mark.

Day 7:

The conditions were dry due to 2 days without heavy rain. The plants had grown an additional inch or two and seemed quite healthy. The windburns were nowhere near as noticeable as on Day 4.

There was still some Bacterial Spot visible, and it was rated at about 3%. Part of the infection was present on old growth which probably didn't get any coverage, and one or two new growth plants looked like they had the beginnings of Bacterial Spot. However, it was very difficult to determine due to the small size of the damage on the leaves, and could have been insect damage, but was rated as Bacterial Spot. Stem Rot was still present on 5% of the plants, and Blight was present on 1%.

CONCLUSION

This particular field sits at the top of a canyon and is planted on rolling and undulating soil. There are pockets of lower points that receive very little wind, and there are also higher points that receive high winds which carry, when raining, an incredible amount of water at high velocity. The grower and his father have been farming for 40 years and in their words "this was the worst year for rain ever." Disease pressure was worse in this field than the present inventor has witnessed to date. Indeed, the grower had previously stated, in his own words, that "We almost gave this field up for dead."

The grower gave the Treatment a 4 on a scale of 1 (Poor) to 5 (Perfect), when compared to hydrogen peroxide. H is rating for hydrogen peroxide was 2.5 to 3. The grower did not rank the treatment a perfect score due to the fact he didn't have the product on the crop over a longer period of time to evaluate its consistency, but indicated that he was very happy with the product and had confidence in it after it took his poor conditioned crop and turned it viable once again. He also indicated that he was most impressed with the amount of new growth after he put the product on and how quickly the plants responded.

In fairness, the grower does not like using hydrogen peroxide. The health hazards when using hydrogen peroxide in a windy area are not worth it to him although he has had the product in his rotation.

The Dithane treated area was not in good shape. The diseases were responding (especially on molds and mildews) but not as rapid and completely. The present diseases were stressing the plants and they weren't growing at a great rate.

As for putting the product in his rotation, the grower indicated a strong willingness to do so. He felt that the product handled a large array of diseases where some of his other products are more pointed.

SUMMARY

The treatment was superior to the commercial products hydrogen peroxide and Dithane in this field trial, on three different fields, giving very good control of many fungal and bacterial pathogens. There was no phytotoxicity observed, and the product was well liked by the grower.

EXAMPLE 5

Trial of the Quat Salts on Green Peppers

Two separate trials were conducted on two different farms. The same composition as used in Example 4 was applied to mature bell pepper plants that had an established bacterial infection.

The first trial was applied in Florida on mature bell pepper plants the third week of April 2005. The field suffered from a severe bacterial infection and damage. Prior to the application, the grower was considering removing the damaged crop and re-planting due to the extent of the bacterial damage. The treatment was applied twice, with the second application applied 17 days after the first. The treatment was used at a rate of 1:100 in a tank mix. The first spray was with Kocide and the second was the treatment alone. There were no compatibility issues with the tank mix with Kocide.

The Treatment results were very good. The crop showed definite signs that the bacteria had stopped its spread, and very few new bacterial infections were observed. The grower said he could tell a difference a few days after the first spray, namely, that with the treatment, the bacteria had stopped progressing. The grower also noted that the mature plants had a flush of new growth a week after the fist spraying.

The second treatment trial was applied the first week of May, 2005, on mature peppers about one week from harvesting. It rained most of the days in the afternoons. The plants had had an outbreak and the grower wanted to try to save at least part of his crop. Only one application was made on the infected block and the two blocks on either side of the infected block. The application resulted in the bacteria remaining in check and not spreading to the non-infected blocks. This demonstrated that the treatment had preventative affects, as continued sprays were not needed to finish the crop.

With respect to the above description then, it is to be realized that the optimum formulation for this invention, to include variations in emulsion size, dispersants, surfactants, humectants, thickening agents, and biocides are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A composition comprising
about 400 ppm dicocodimethylammonium chloride
about 1200 ppm EDTA;

about 3000 ppm soybean oil;
about 180 ppm of at least one emulsifier;
about 400 ppm citric acid; and
about 40 ppm soyamine.

2. The composition of claim 1, wherein the emulsifier is sorbitol monooleate or nonylphenolethoxylates.

3. A method of treating bacterial or fungal blight comprising
applying the composition of claim 1 to at least one infected plant.

4. The method of claim 3, wherein the composition is applied at a rate of 1 gallon/100 gallons of water/acre.

5. The method of claim 3, further comprising the step of applying diathane before applying the composition.

6. The method of claim 5, wherein the step of applying diathane is carried out at least five days prior to application of the composition.

\* \* \* \* \*